United States Patent
Raju et al.

(10) Patent No.: US 11,185,311 B2
(45) Date of Patent: Nov. 30, 2021

(54) DISTINGUISHING LUNG SLIDING FROM EXTERNAL MOTION

(71) Applicant: KONINKLIJKE PHILIPS N.V., Eindhoven (NL)

(72) Inventors: Balasundar Iyyavu Raju, North Andover, MA (US); Jingping Xu, Shanghai (CN); Shougang Wang, Ossining, NY (US); Shiwei Zhou, Acton, MA (US); Anthony M. Gades, Snohomish, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 686 days.

(21) Appl. No.: 15/760,244

(22) PCT Filed: Sep. 13, 2016

(86) PCT No.: PCT/IB2016/055430
§ 371 (c)(1),
(2) Date: Mar. 15, 2018

(87) PCT Pub. No.: WO2017/046692
PCT Pub. Date: Mar. 23, 2017

(65) Prior Publication Data
US 2018/0344293 A1  Dec. 6, 2018

Related U.S. Application Data
(60) Provisional application No. 62/219,686, filed on Sep. 17, 2015.

(51) Int. Cl.
*A61B 8/00* (2006.01)
*A61B 8/08* (2006.01)
(Continued)

(52) U.S. Cl.
CPC ............ *A61B 8/54* (2013.01); *A61B 8/085* (2013.01); *A61B 8/4254* (2013.01); *A61B 8/463* (2013.01);
(Continued)

(58) Field of Classification Search
CPC combination set(s) only.
See application file for complete search history.

(56) References Cited

U.S. PATENT DOCUMENTS 5,529,070 A    6/1996  Augustine et al.
5,782,766 A *  7/1998  Weng ............... G06T 7/246
                                                128/916

(Continued)

FOREIGN PATENT DOCUMENTS

WO    2008073560 A2    6/2008
WO    2013088326 A2    6/2013
WO    2016046140 A1    3/2016

OTHER PUBLICATIONS

Alrajhi et al: "Test Characeristics of Ultrasonography for the Detetion of Pneumothorax:A Systematic Review and Meta-Analysis"; Chest, 141/3. Mar. 2012, p. 703-.

(Continued)

*Primary Examiner* — Joel F Brutus

(57) ABSTRACT

Extracorporeal motion (130) relative to a medical subject being imaged is detected, through the imaging or from motion detectors on the imaging probe, and either backed out of the medical images so that it can be determined whether lung sliding exists or measured to determine whether lung sliding detection is to be suspended due to excessive extracorporeal motion. Image sub-regions (164, 168) corresponding to respective ones of the images are selected for image-to-image comparison such that the selected sub-regions contain only body tissue that is, with respect to imaging depth in the acquiring of the images, (Continued)

shallower than an anatomical landmark within the images. Based on a result of the comparing, lung sliding detection that entails examining image data deeper than the landmark may be initialized. A motion sensor may detect the extra-corporeal motion and, based on its output: pair-wise co-register (170) images to an extent of backing out the effect of the extracorporeal motion and/or determine whether to suspend deciding as to whether lung sliding is, during the respiration, occurring in the subject.

14 Claims, 3 Drawing Sheets

(51) Int. Cl.
G01S 7/52 (2006.01)
G01S 15/89 (2006.01)

(52) U.S. Cl.
CPC ........ *A61B 8/5276* (2013.01); *G01S 7/52077* (2013.01); *G01S 15/892* (2013.01)

(56) References Cited

U.S. PATENT DOCUMENTS

| 6,511,426 | B1 | 1/2003 | Hossack et al. |
| 6,589,176 | B2 | 7/2003 | Jago et al. |
| 2011/0274334 | A1* | 11/2011 | Zhu ........................ G06T 7/248 382/132 |
| 2013/0158365 | A1* | 6/2013 | Chey ...................... A61B 5/227 600/301 |
| 2013/0184584 | A1* | 7/2013 | Berkey ................. A61B 8/4444 600/441 |
| 2013/0197370 | A1* | 8/2013 | Burlina ................. A61B 6/5217 600/476 |
| 2015/0133786 | A1* | 5/2015 | Wong ................... A61B 8/4427 600/441 |

OTHER PUBLICATIONS

Ball et al: "The Occult Pneumothorax: What Have We Learned?" Can J. Surg, vol. 52, No. 5, Oct. 2009, E173-E179.

Ku et al: "Clinician-Perofrmed Beside Ultrasound for the Diagnosis of Traumatic Pneumothorax"; Western Journal of Emergency Medicine, vol. XIV, No. 2, Mar. 2013, pp. 103-108.

Volpicelli et al: "International Evidence-Based Recommendations for Point-Of-Care Lung Ultrasound"; Intensive Care Med (2012), 38, pp. 577-591.

Oveland et al: "The Intrapleural Volume Threshold for Ultrasound Detetion of Pneumothoraces:An Experimental Study on Porcine Models"; Scandinavian Journal of Trauma, Resuscitation & Emergency Medicine, 2013, 21:11, 7 Page Article.

Perera et al: "Rapid Ultrasound in Shock:The Rush Protocol"; Emergency Ultrasound, Apr. 2010, pp. 12-14.

Perera et al: "Rapid Ultrasound in Shock:The Rush Protocol"; Emergency Ultrasound, May 2010, pp. 24-26.

McClean et al: "Ultrasound Determination of Chest Wall Thickness:Implications for Needle Thoracostomy"; American Journal of Emergency Medicine (2011) 29, pp. 1173-1177.

* cited by examiner

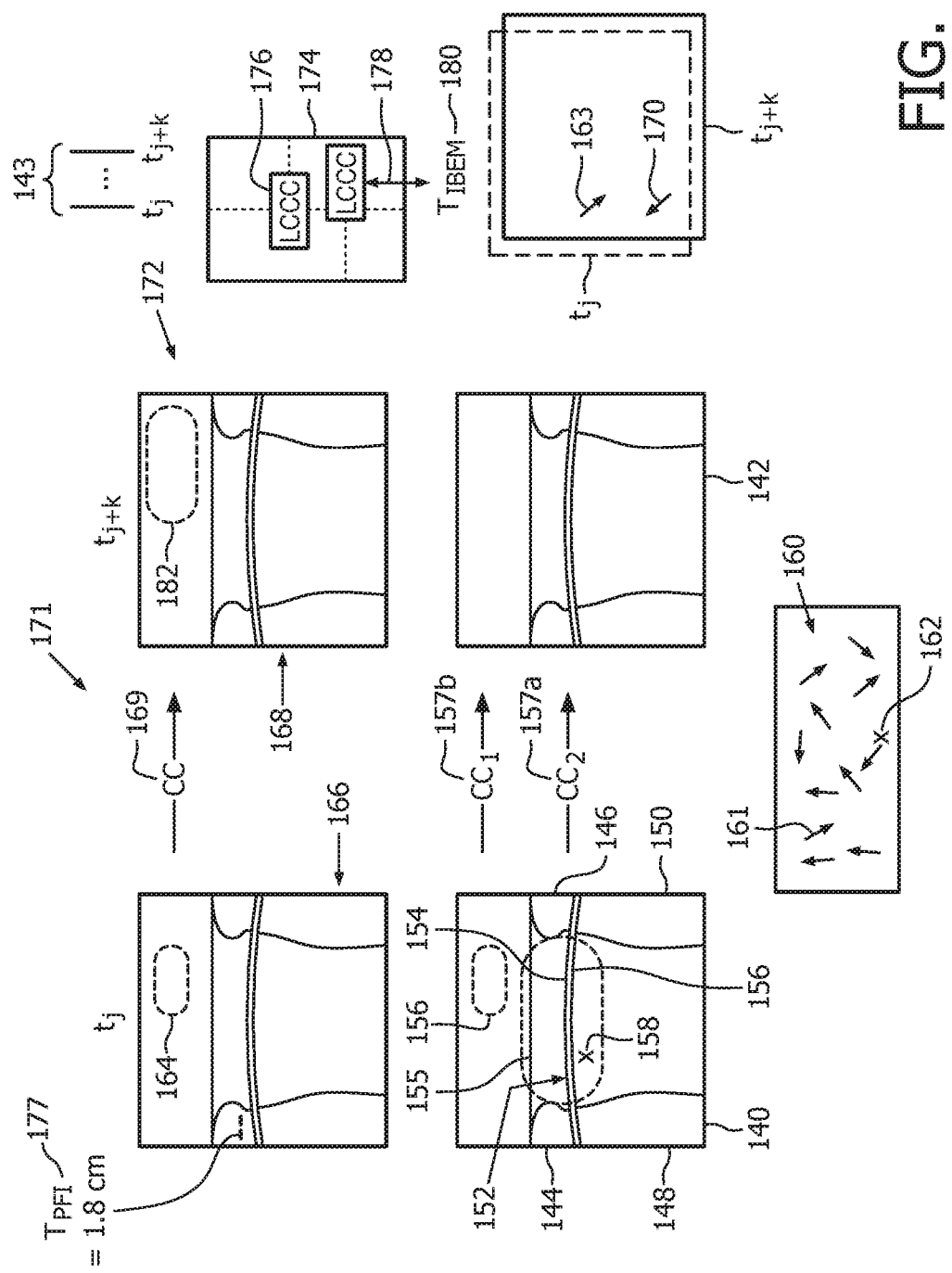
FIG. 1-II

DISTINGUISHING LUNG SLIDING FROM EXTERNAL MOTION

This application is the U.S. National Phase application under 35 U.S.C. § 371 of International Application No. PCT/M2016/055430, filed on Sep. 13, 2016, which claims the benefit of U.S. Provisional Application Ser. No. 62/219,686, filed Sep. 17, 2015. These applications are hereby incorporated by reference herein.

FIELD OF THE INVENTION

The present invention relates to using imaging to detect a pneumothorax and, more particularly, to such detection in the presence of external motion.

BACKGROUND OF THE INVENTION

Worldwide, chest trauma accounts for 20% of all traumas. Early diagnosis and timely selection of the appropriate treatment are critical components for optimal outcome. Medical imaging plays an important role in the decision-making process. Among blunt chest trauma cases, pneumothorax (PTX) represents the second most common injury, after rib fracture. PTX may occur as a result of blunt or penetrating trauma. Small PTXs are usually asymptomatic and can safely be managed without a chest drain, provided the patient does not need mechanical ventilation or air transportation. In these cases, any size PTX should be treated with a thoracotomy tube to avoid the creation of tension PTX. Large PTXs may cause respiratory distress, and tension PTXs can cause cardiorespiratory failure. In tension PTX, air leaks into the pleural cavity with no escape route, on account of a one-way valve effect and is a life-threatening condition.

While computed tomography (CT) is considered the gold standard in PTX detection and measurement of its volume, the major problem for CT is that it cannot be performed on unstable patients at bedside. Chest X-ray done at bedside (anteroposterior supine chest radiography in particular) can miss up to 30% of PTX cases. One study found that the sensitivity of chest X-ray for diagnosing PTX is low even when PTX volume is sizable (350 ml to 500 ml).

Ultrasound imaging, especially Point-of-Care Ultrasound (POC-US), is an imaging modality becoming more commonly used for bedside detection of PTX. However, the major problem with ultrasound examination is the need for training and the high operator dependence of examination outcomes. A contributing factor is a new class of users who typically are not training specifically to become sonographers. One study showed that inexperienced users could only achieve an average sensitivity of 57%, compared to an average sensitivity of 90.9% for experienced users of ultrasound imaging in PTX detection.

In a normal lung, a high frequency linear array transducer or curved array is positioned at the most anterior point of the chest to identify the pleural line. This line appears as an echogenic horizontal line, located approximately a half-centimeter deeper than the shallowest extent of the ribs. The pleural line consists of the closely opposed visceral and parietal pleura. In a normal lung, the visceral pleura can be seen sliding back and forth against the parietal pleura producing a physiological phenomenon called "lung sliding", with a glistening or shimmering appearance as the subject breathes. B-line or B-lines artifacts (also called 'comet-tail' artifacts) are vertical hyperechoic lines that may extend posteriorly from the opposed pleura to the bottom of the screen or maximum imaging depth. Usually it is possible to identify the ribs both superiorly and inferiorly, and from there to locate the pleural line between two ribs in the horizontal direction. The presence of lung sliding and vertical B-line or B-lines rules out PTX.

In the case of PTX with large free air, air accumulates between the layers of the parietal and visceral pleura and splits the two layers apart. The accumulation of air, where it exists, prevents the ultrasound beam from propagating through the lung. Correspondingly, there is no lung sliding or B-line/B-lines. The pleural line will consist only of the parietal layer, seen as a single stationary line.

In the case of PTX with a moderate or smaller amount of free air, there exists partial normal lung, and a partial abnormal portion with PTX. In this situation, there could be a lung-point between the two parts. Here, lung sliding may be noted laterally but not anteriorly, as free air will preferentially collect superiorly and anteriorly within the chest cavity. The lung point of transition between the area of lung sliding and the absence of sliding may be detected by looking at the pleural line in several intercostal spaces.

U.S. Pat. No. 8,914,097 to Burlina et al. ("the Burlina patent"), the entire disclosure of which is incorporated herein by reference, detects lung sliding by computing vectors of inter-image motion for images acquired at different times, each image including a pleural interface. The vectors form a field across the entirety of each image. Probe translation can be detected from agreement among vectors as to direction and magnitude. According to the Burlina patent, probe motion identified is prevented from affecting PTX detection. The Burlina patent mentions that motion observations may be combined for greater robustness, but does not otherwise suggest or specify how the adverse impact on PTX detection might be prevented.

SUMMARY OF THE INVENTION

What is proposed herein below is directed to addressing one or more of the above-discussed concerns.

In certain aspects, the present invention includes, an imaging system (100) configured to detect lung sliding. The imaging system can include an ultrasound probe having a lens surface; and a processor configured to perform the following steps: select a first sub-region (164) in a first ultrasound image and a second sub-region (182) in a second ultrasound image, the first and second sub-regions comprising image data representing tissue in the subject that is closer to the lens surface than an anatomical landmark within the first and second ultrasound images; estimate an effect of extracorporeal motion in a subject by comparing relative alignment between the first and second sub-regions; and determine whether to suspend imaging of lung sliding in said subject based on a magnitude of the effect of extracorporeal motion. The system can include a motion sensor attached to said probe. In some aspects, the comparing relative alignment can include comparing positional data from the motion sensor for the first and second sub-regions.

In some aspects, extracorporeal motion entails movement of the lens surface with respect to a portion (128) of a skin surface of the subject within a period (143) of time spanned by acquiring the first and second ultrasound images. The system can include a display (115) configured to display a spatial map of similarity between the first and second sub-regions. The spatial map of similarity can be based on a cross-correlation of image data between the first and second sub-regions. The processor can be configured to determine whether to suspend imaging based on a first motion threshold of relative alignment between the first and second sub-regions. The processor can also be configured to issue a user notification indicating whether to suspend imaging of lung sliding. The user notification can, e.g., include a binary indicator (S256). In some aspects, the first and second sub-regions (164, 182) are predefined so as to be shallower than a depth threshold (177) corresponding to a distance away from the lens surface. The depth threshold (177) can be no greater than 1.8 centimeters. In certain aspects, the anatomical landmark comprises a pleural line (152). The spatial map can include a plurality of local correlation coefficients. In some aspects, if the first motion threshold is exceeded, the processor is configured to suspend imaging of lung sliding. The display can also be configured to display a bar having a length indicative of the likelihood of lung sliding based on the relative alignment between the first and second sub-regions.

In some aspects, the present invention includes an imaging scanner is configured for detecting lung sliding and, more particularly, for acquiring images from a subject at different times during respiration. The scanner can include:
a) circuitry configured for, to detect extracorporeal motion relative to the subject, selecting image sub-regions corresponding to respective ones of the images for image-to-image comparison such that the selected sub-regions contain only body tissue that is, with respect to imaging depth in the acquiring, shallower than an anatomical landmark within the images and for, based on a result of the comparing, initializing, for the lung sliding detection, examination of image data deeper than the landmark; and/or
b) both a motion sensor to detect the extracorporeal motion and circuitry configured for, based on output of said sensor:
 i) estimating an effect of the extracorporeal motion on relative alignment between a pair of the images; and, to an extent of backing out the estimated effect, pair-wise co-registering for deciding, based on comparison between both constituents of the co-registered pair, whether lung sliding is occurring in the subject during respiration; and/or
 ii) determining whether to suspend deciding as to whether lung sliding is, during the respiration, occurring in the subject.

A corresponding method and a corresponding computer readable medium are also proposed herein below.

Details of the innovative scanner with lung sliding detection initialization capability are set forth further below, with the aid of the following drawings, which are not drawn to scale.

DETAILED DESCRIPTION OF EMBODIMENTS

Figure 1:
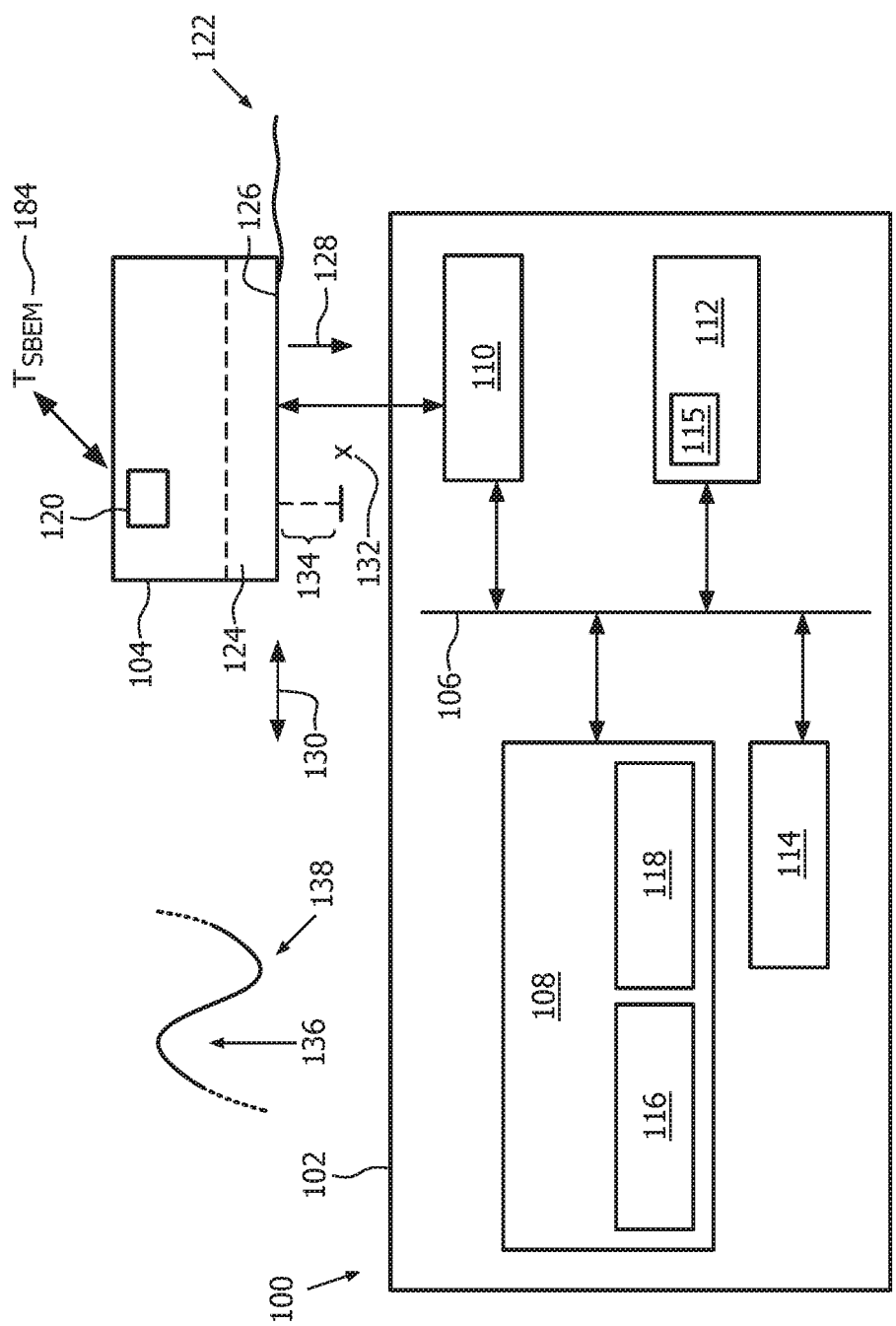
FIG. 1 is a schematic diagram of an exemplary, innovative imaging system with lung sliding detection initialization capability, which diagram further illustrates related concepts in the context of the present invention.

FIG. 1 shows, by way of illustrative and non-limitative example, an imaging scanner or imaging system 100 with lung sliding detection initialization capability. Typically, the scanner 100 would have a complete lung sliding detection capability, as well. The scanner 100 includes an image analyzer 102 and an imaging probe 104. The imaging modality may be ultrasound, and is assumed in the embodiments described herein below. However, other medical imaging modalities may be used instead. For example, a portable magnetic resonance imaging (MRI) device in an ambulance may produce images that are adversely affected by patient-to-coil motion caused by ambulance motion.

The image analyzer 102 includes, on a data and power bus 106, processing circuitry 108, a device interface 110, a user interface 112, and a PTX detector 114. The user interface 112 includes a display 115 and user input controls (not shown).

The processing circuitry 108 can include a memory 116 and a processor 118. As described further herein, the processor can be configured to perform the following steps: select a first sub-region in a first ultrasound image and a second sub-region in a second ultrasound image, the first and second sub-regions comprising image data representing tissue in the subject that is closer to the lens surface than an anatomical landmark within the first and second ultrasound images; estimate an effect of extracorporeal motion in a subject by comparing relative alignment between the first and second sub-regions; and based on the effect of extracorporeal motion, determine whether to suspend imaging of lung sliding in said subject.

The probe 104 may include one or more motion sensors 120. The latter are incorporated within the probe 104 or are otherwise physically attached to the probe. An implementation that incorporates within the probe 104 is described in connection with FIGS. 5 and 5a in commonly-assigned U.S. Pat. No. 5,529,070 to Augustine et al. ("Augustine"), the entire disclosure of which is incorporated herein by reference.

However, the imaging itself may be used, instead of or in addition to, any such sensors 120, in accordance with what is proposed herein with regard to extracorporeal motion detection or correction.

The probe 104 may be manually held against the skin surface of a subject 122, such as a human or animal patient. The probe 104 includes a transducer 124, such as a one- or two-dimensional transducer array having a face 126. Imaging is performed across the face 126 in a range direction 128 of the probe 104 which is a direction orthogonal to the azimuthal and elevation directions. A layer of acoustic gel is often the medium used to separate the face 126 from a portion 128 of the skin surface. Through inadvertent hand motion relative to the skin surface portion 128, or more generally relative to the subject 122, the imaging may be rigidly moved, as represented by the double headed arrow 130 in FIG. 1. Hand or patient movement, caused by ambulance motion, may create the rigid movement in the imaging. The probe 104 may also be moved in a direction normal to the drawing sheet, rocked in the plane of the drawing sheet, rocked around an axis in the plane of the drawing sheet, or twisted around the orthogonal axis within the plane. Any of the communication between the probe 104 and the image analyzer 102, or among any of the components 108-114 of the image analyzer, could be implemented as wired or wireless connections.

The processing circuitry 108, device interface 110, user interface 112, and PTX detector are implementable with the lung sliding detection functionality described in: a) the commonly-owned, PCT Application PCT/EP2015/071625, entitled "Device and method for automatic pneumothorax detection" to Jinping Xu et al. ("the Xu application") in which all of the inventors are inventors in the instant patent application, having an effective filing date of Sep. 25, 2014, the entire disclosure of which is incorporated herein by reference; or b) the Burlina patent. In addition, other circuitry is included, in for example the processing circuitry 108 and the PTX detector 114, for enabling the lung sliding detection initialization capability. Circuitry referred to herein may be described as configured to perform a function. The configuration is understood to be, for example, either through hard wiring or by virtue of stored capacitive charges representative of instructions or of data. For example, execution of instructions in realizing functionalities for sliding motion analysis configures processing circuitry.

The scanner 100 images the subject 122 via ultrasound received, and in a pulse-echo context also emitted, by the probe 104. Image data 132 acquired is at a respective imaging depth 134, in the range (or "axial") direction 128, from the probe 104. The imaging occurs during respiration of the subject 122, made up of cycles of inhalation 136 and exhalation 138.

Some existing approaches to automated PTX detection are as follows.

In the Xu application, the imaging may be acquired as frames 140, 142 of image data 132.

In the first exemplary frame 140 in FIG. 1, a superior rib 144 and an inferior rib 146 are seen for a normal lung. At greater imaging depth 134, shadows 148, 150 result from the ultrasound absorption by the ribs 144, 146. A pleural line 152 which is an anatomical landmark consists, in a normal lung, of the closely opposed parietal pleura 154 and visceral pleura 156.

In the case of PTX or incomplete PTX, the two pleura 154, 156 are separated more distantly away from each other by air longitudinally disposed between the ribs 144, 146 for, correspondingly, the entire length or for part of the length. In the latter case, a lung point exists, i.e., where the separation becomes abnormal. Accordingly, when PTX exists, the pleural line 152 consists of the parietal pleura. When incomplete PTX exists, the pleural line 152 consists of only the parietal pleura where air forces apart the two pleura 154, 156, and of both pleura where they are closely opposed.

The second frame 142 is acquired at a different, subsequent time.

Problematically, extracorporeal motion 130 relative to the subject 122 that affects the imaging may have occurred within a time period 143 that spans the acquisition times $t_j$, $t_{j+k}$ of frames 140, 142 being compared with each other, that comparison intending to assess possible motion along the pleural line 152 that is indicative of the presence or absence of lung sliding.

The Xu application defines a first sub-region 155 covering the part of the pleural line 152 between the ribs 144, 146. A second sub-region 156 is defined which contains only background soft tissue whose imaging depth 134 is shallower than the pleural line 152. For the frames 140, 142 being compared, relative motion between the two sub-regions 155, 156 is measured. This is based on the key insight that, despite possible lung sliding and other internal motion, the region above the pleural line 152 would be seen in the imaging as stationary, when there is no extracorporeal motion 130 relative to the subject 122, such as inadvertent hand motion; however, such motion that displaces the imaging with respect to the subject 122 would cause that region to appear to be moving in the imaging. Accordingly, relative motion is assessed to detect lung sliding if any, thereby reducing an adverse impact of the extracorporeal motion 130. Relative motion can be calculated from two cross-correlations 157a, 157b, one using the first sub-region 155 and the other using the second sub-region 156. It is noted that the first sub-region 155 contains tissue 158 having an imaging depth 134 deeper than the pleural line 152.

The Burlina patent forms, as mentioned herein above, a field 160 of motion vectors 161 over the entirety of the images being compared. According to the Burlina patent, probe motion identified is prevented from affecting PTX detection. The Burlina patent mentions that motion observations may be combined for greater robustness, but does not otherwise suggest or specify how the adverse impact on PTX detection might be prevented. It is likewise noted here that the Burlina patent includes motion vectors relating to tissue 162 having an imaging depth 134 deeper than the pleural line 152. Motion vector estimation is problematic for the Burlina technique when the signal-to-noise ratio (SNR) is weak under the pleural line.

Advantageously in accordance with what is proposed herein, the automated deciding on whether PTX is present is either postponed during detected periods of extracorporeal motion 130 or the effect 163 of such motion on relative alignment between acquired images is backed out as an initialization of the decision process.

In particular and by way of example, an "earlier" sub-region 164 of frame 166 is selected which is similar to the second sub-region 156 of the Xu application. In some embodiments, a processor of the imaging system is configured to select a first sub-region (164) in a first ultrasound image and a second sub-region (182) in a second ultrasound image, the first and second sub-regions comprising image data representing tissue in the subject that is closer to the lens surface than an anatomical landmark within the first and second ultrasound images. For example, the frames 166, 168 of the pair are cross-correlated 169 using the sub-region 164. Pair-wise alignment (or "co-registration") 170 of the frames 166, 168 by, for instance, shifting one of them relative to the other, as a correction, using the optimal lag(s) serves as an initialization 171 for the Xu scheme and/or for the Burlina scheme. The initialization 171 improves the SNR for either scheme.

As another example, the values in a spatial map of local cross-correlations (LCCs) on an entire upper part of the frames 166, 168 of sufficient shallowness may suggest postponing application of the Xu or Burlina scheme until the extracorporeal motion 130 sufficiently subsides.

For a one-dimensional transducer array, extracorporeal motion 130 relative to the subject 122 might result in unintended motion in the lateral and axial directions the effect 163 of which can be backed out by the alignment 170 of one the images $t_j$, $t_{j+k}$ with other, thereby effecting the initialization 171.

In the case of a two-dimensional transducer array, unintended motion may, in addition, be measured in the orthogonal, i.e., elevation, direction by use of a three-dimensional cross-correlation.

The cross-correlation coefficient may be a Pearson product-moment correlation coefficient. It could be a normalized correlation coefficient. It is well-known in the field of ultrasound imaging that the normalized correlation function indicates the correlation of the ultrasound data at a corresponding point in the sequence of temporal frames as a function of time as well as relative displacement of the corresponding point in the sequence. The cross-correlation coefficient could also be based simply on the sum of squared differences.

Figure 2:
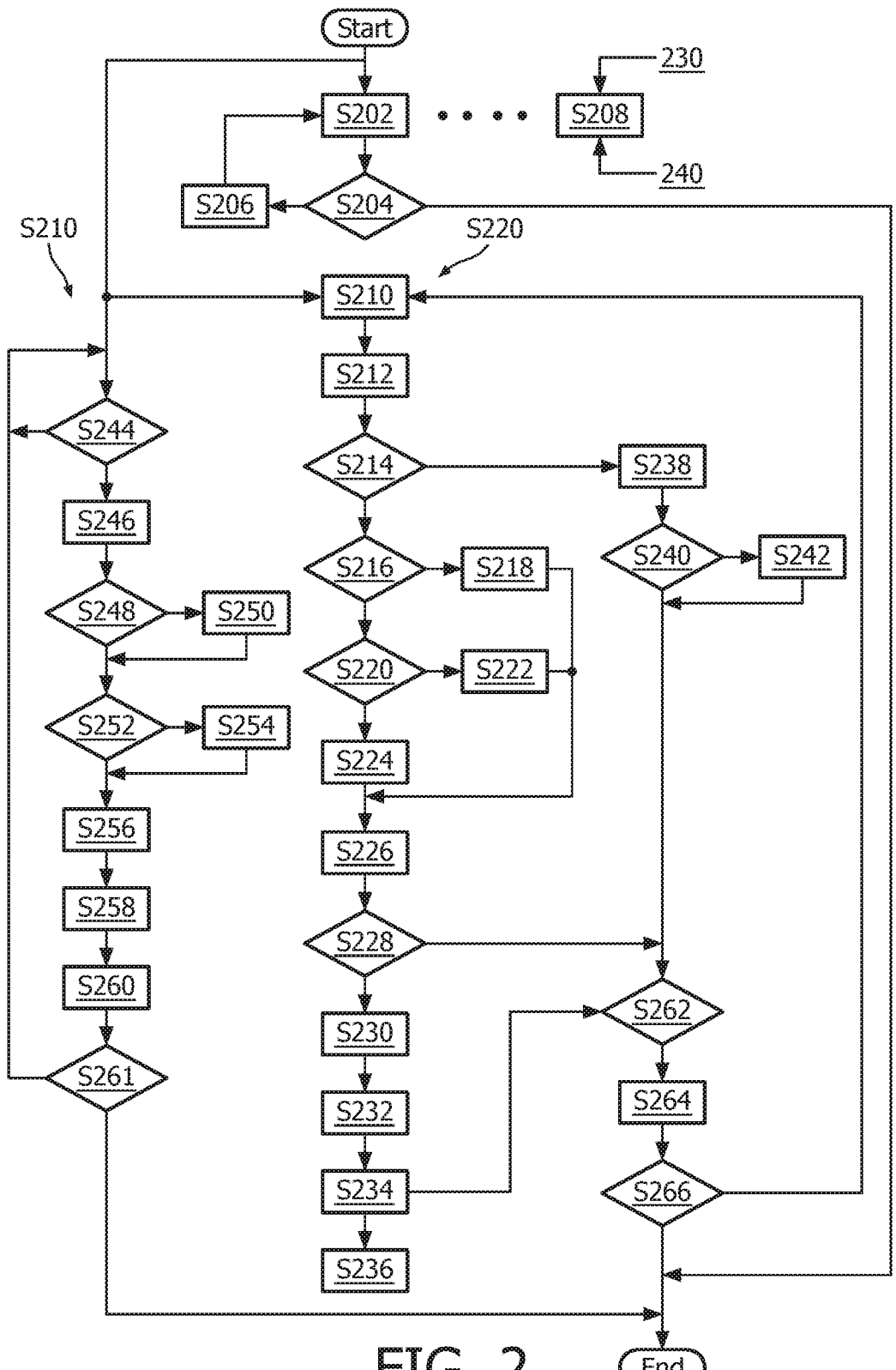
FIG. 2 is a flow chart shows an exemplary operation in accordance with the present invention.

Operationally, as seen in the example provided by FIG. 2, images are acquired, via the probe 104, at respiration times $t_1$ (step S202). While image acquisition continues (step S204), the index i is incremented with each image acquired (step S206).

Launched concurrently are a PTX detection regulation process 210 and a PTX detection pre-correction process 220.

Also simultaneous with image acquisition, the probe 104 may be manually held in place against the skin surface portion 128 of the subject 122 (step S208). Accordingly, inadvertent hand motion 230 can affect the imaging. Even if the probe is robotically held in place, ambulance motion 240 in a portable application may, likewise, introduce extracorporeal motion 130 with respect to the subject 122.

In the PTX detection pre-correction process 220, images $t_j$ and $t_{j+k}$ are selected (step S210). Here, k can be 1, representing the next image acquired, or k can be greater than 1; thus, the two images are acquired at different times during the respiration of the subject 122. The circuitry 108 compares the pair 172 of images $t_j$, $t_{j+k}$ in forming a spatial map 174 of local indications of similarity between the constituent images $t_j$ and $t_{j+k}$ of the pair 172 (step S212). In some aspects, the spatial map of similarity is based on a cross-correlation of image data between the first and second sub-regions of ultrasound images. A local indication, in this context, may be a local cross-correlation coefficient (LCCC) 176 derived by cross-correlating a small, local area, such as 8 pixels. Each entry of the map 174 corresponds to a center pixel of the 8 used for that entry. The LCCC 176 is thus a type of similarity-indicator-magnitude metric. The image data 132 subjected to the comparison, e.g., cross-correlation, is radiofrequency (RF) data. However, other data such as envelope detected data or Digital Imaging and Communications in Medicine$^T$ (DICOM) image data, may be used as well.

If correction is image-based (step S214), rather than motion-sensor-based, the processing path depends on how shallow parts of the pair 172 of images $t_j$ and $t_{j+k}$ are to be identified. For example, comparing relative alignment can include comparing positional data from the motion sensor for the first and second sub-regions in the ultrasound images.

If the correction is image-based and a predefined cutoff based on the imaging depth 134 is to be used (step S216), the cutoff must meet a shallowness criterion, i.e., minimum degree of shallowness (step S218). The pleural line 152 is typically around 2 centimeters (cm) from the skin surface in adult humans. Therefore, frame data above 1.5 cm, or even 1.8 cm for instance, can be examined. The cutoff thus occurs at a patient-independent and temporal-imaging-frame-independent threshold $T_{PFI}$ 177 of for instance 1.8 cm or less. Optionally, it may not be assumed that the pleural line 152 is at a particular depth.

Thus, if a predefined cutoff is not used (step S216), the pleural line 152 is to be located. Processing depends on whether pixel brightness detection from the pair 172 of images $t_j$ and $t_{j+k}$ is employed (step S220).

If pixel brightness detection is to be employed (step S220), features such as high brightness lines around the 2 cm mark or lower can be detected (step S222). The Burlina patent, for example, discloses combining a Hough transform with a form of brightness thresholding. However, other anatomical structures, such as muscle fibers, may appear as bright lines.

Another approach, used in the Xu application, is based on filtered forms of the map 174 and of the pair 172 of images $t_j$ and $t_{j+k}$. If this approach is used, processing follows the technique disclosed in the Xu application (step S224). This approach could, to reduce processing, be implemented in simplified form that finds the pleural line 152, at least in some cases, by detecting an abrupt change in local spatial similarity indicators, such as cross-correlation coefficients 176. With one dimension of the map 174 corresponding to the range direction 128, scanning proceeds in that direction for the abrupt change, and the process is iteratively done by shifting the scanning in a direction perpendicular to the range direction. The set of abrupt changes laterally correspond to the pleural line 152.

Once the necessary degree of shallowness is determined from one or more of the methods just discussed, the LCCCs 176, or more generally at least one similarity-indicator-magnitude metric derived using a magnitude from among the one or more magnitudes of a respective one or more similarity indicators, for a shallow part of the pair 172 are compared 178 to an imaging-based extracorporeal motion threshold $T_{IBEM}$ 180 (step S226). The part is shallow enough so that its imaging depth 134 is everywhere less than that of the pleural line 152. The part is defined by selecting the earlier sub-region 164 in the earlier frame 166. The earlier sub-region 164 contains only body tissue shallower than the anatomical landmark, i.e., the pleural line 152. The threshold $T_{IBEM}$ 180 may have a value close to unity.

If, for example, a predefined percentage, or more, of the LCCCs 176 are smaller than the threshold $T_{IBEM}$ 180 (step S228), this indicates that substantial extracorporeal motion 130 exists. In this case, the previously-described earlier sub-region 164 of the earlier frame 166 is selected, and a later sub-region 182 of the later frame 168 is selected which is larger than, and encompasses, the selected earlier sub-region 164 (step S230). The two frames 166, 168 are cross-correlated based on their respective sub-regions 164, 182 (step S232). Since the sub-regions 164, 182 reside shallower than the pleural line 152, where the body tissue remains motionless, the cross-correlation estimates the effect 163 of the extracorporeal motion 130 on relative alignment between the constituent images, of the pair 172, that are being mutually compared. It is noted that, alternatively, the larger sub-region can be selected from the earlier frame 166, with the two frames 166, 168 being correspondingly cross-correlated. One or more minimal lags are found from the cross-correlation (step S234). The two sub-regions 164, 182 are then co-aligned 170, thereby aligning the two frames 166, 168 and, thus, the pair 172 of images $t_j$ and $t_{j+k}$ to the extent of backing out the effect 163 of the extracorporeal motion 130 (step S236).

If, on the other hand, correction is motion-sensor-based (step S214), sensor output is compared to a sensor-based extracorporeal motion threshold $T_{SBEM}$ 184 (step S238).

If the sensor output falls below $T_{SBEM}$ 184 (step S240), the constituent images $t_j$ and $t_{j+k}$ of the pair 172 are co-aligned (or "co-registered") 170 to the extent of backing out the effect 163 of the motion detected via the motion sensor(s) 120 (step S242).

As to the PTX detection regulation process 210, when the one or more minimal lags in step S234 or the motion sensor output in step S238 becomes available (step S244), they may be compared to respective motion thresholds in real time as they become available (step S246). Accordingly, any image- or sensor-based thresholding may be performed with, for example, the same frame rate as that of an ultrasound B-mode scan. If respective first motion thresholds are exceeded (step S248), lung sliding detection is suspended, or any such suspension is maintained (step S250). If respective second motion thresholds are not attained (step S252), lung sliding detection is enabled or, if currently suspended, removal of suspension is either effected or considered (step S254). Consideration might take into account whether the extracorporeal motion 130 has been sufficiently low for at least a minimal period of time. The first and second motion thresholds might or might not be identical. On the display 115, a binary indication of enablement or suspension of lung-sliding detection can be shown (step S256). Alternatively or in addition, other user feedback is possible, such as auditory feedback. The feedback can help the user handling the probe 104 to keep it steady. Another item that can be displayed is a bar whose length is indicative of the likelihood of lung sliding (step S258). The probability of lung sliding can be determined from a hidden Markov model, as described in the Burlina patent. Also, the map 174 implemented, for instance, to display LCCCs 176 can be shown on-screen and updated in real time (step S260). Any of the user feedback in steps S256-260 can be updated in real time, e.g., at the same frame rate as that of an ultrasound B-mode scan. If processing is to continue (step S261), a branch back to step S244 is made to reiterate the PTX detection regulation process 210.

On the other hand, if the image-based threshold $T_{IBEM}$ 180 is met or exceeded (step S228), if the sensor output meets or exceeds sensor-based $T_{SBEM}$ 184 (step S240), if less than the predefined percentage of the LCCCs 176 are smaller than the threshold $T_{IBEM}$ 180, or if the pair 172 of images $t_j$ and $t_{j+k}$ is, to back out the effect 163 of the extracorporeal motion 130 relative to the subject 122, pair-wise co-registered 170 based on the imaging (step S236) or on the sensor output (step S242), processing depends on whether lung sliding detection is currently enabled (step S262). It is initially enabled by default, but subject to change in accordance with steps S248-S254. If it is currently enabled (step S262), the pair 172 of images, already co-registered to an extent of backing out the effect 163 of the extracorporeal motion 130 relative to the subject 122, is subject to automated comparison between the constituent images of the pair in accordance with either the Xu application or the Burlina patent for example (step S264), to automatically decide whether lung sliding is occurring in the subject during respiration 136, 138. If processing is to continue (step S266), a branch back to step S210 is made to reiterate the PTX detection pre-correction process 220.

The PTX detection pre-correction process 220 can include imaging-based pre-correction (step S214), sensor-based pre-correction, or both. In any of the three cases, the PTX detection regulation process 210 may be included.

The scanner 100 is configured for operating automatically without need for user interaction other than holding the probe 104 in step S208.

The scanner 100, as seen from FIG. 2, may be configured to operate in real time. However, acquired imaging can, as in the Burlina patent, be stored in the memory 116 for later use by the processor 118, here in initializing lung sliding detection as well as the detection itself.

What is proposed herein increases the confidence of an inexperienced user of ultrasound in medical emergencies and affords robust PTX detection.

Extracorporeal motion relative to a medical subject being imaged is detected, through the imaging or from motion detectors on the imaging probe, and either backed out of the medical images so that it can be determined whether lung sliding exists or measured to determine whether lung sliding detection is to be suspended due to excessive extracorporeal motion. Image sub-regions corresponding to respective ones of the images are selected for image-to-image comparison such that the selected sub-regions contain only body tissue that is, with respect to imaging depth in the acquiring of the images, shallower than an anatomical landmark within the images. Based on a result of the comparing, lung sliding detection that entails examining image data deeper than the landmark may be initialized. A motion sensor may detect the extracorporeal motion and, based on its output: pair-wise co-register images to an extent of backing out the effect of the extracorporeal motion and/or determine whether to suspend deciding as to whether lung sliding is, during the respiration, occurring in the subject.

It should be noted that the above-mentioned embodiments illustrate rather than limit the invention, and that those skilled in the art will be able to design many alternative embodiments without departing from the scope of the appended claims.

For example, the auditory feedback to help the use hold the probe 104 steady can include spoken instructions.

In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer having a computer readable storage medium and/or by means of an integrated circuit having a machine-accessible storage medium. A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache and RAM. The mere fact that certain measures are recited in mutually different dependent claims does not indicate that a combination of these measures cannot be used to advantage.

What is claimed is:

1. An imaging system configured to detect lung sliding, comprising:
    an ultrasound probe having a lens surface; and
    a processor configured to perform the following steps:
        select a first sub-region in a first ultrasound image and a second sub-region in a second ultrasound image, the first and second ultrasound images comprising image data representing a pleural line, and the first and second sub-regions each consisting of image data representing tissue in the subject that is closer to the lens surface than the pleural line within the first and second ultrasound images;
        estimate an effect of extracorporeal motion in a subject by comparing relative alignment between the first and second sub-regions; and
        determine whether to suspend imaging of lung sliding at the pleural line in said subject based on a magnitude of the effect of extracorporeal motion.

2. The system of claim 1, further comprising a motion sensor attached to said probe.

3. The system of claim 2, wherein the comparing relative alignment comprises comparing positional data from the motion sensor for the first and second sub-regions.

4. The system of claim 1, wherein said extracorporeal motion entails movement of the lens surface with respect to a portion of a skin surface of the subject within a period of time spanned by acquiring the first and second ultrasound images.

5. The system of claim 1, further comprising a display configured to display a spatial map of similarity between the first and second sub-regions.

6. The system of claim 5, wherein the spatial map of similarity is based on a cross-correlation of image data between the first and second sub-regions.

7. The system of claim 6, wherein the processor is configured to determine whether to suspend imaging based on a first motion threshold of relative alignment between the first and second sub-regions.

8. The system of claim 7, wherein if the first motion threshold is exceeded, the processor is configured to suspend imaging of lung sliding.

9. The system of claim 8, wherein the display is configured to display a bar having a length indicative of the probability of lung sliding based on the relative alignment between the first and second sub-regions.

10. The system of claim 5, wherein the spatial map comprises a plurality of local correlation coefficients.

11. The system of claim 1, further comprising circuitry configured to issue a user notification indicating whether to suspend imaging of lung sliding because of extracorporeal motion.

12. The system of claim 11, wherein the user notification comprises a binary indicator.

13. The system of claim 1, wherein the first and second sub-regions are predefined so as to be shallower than a depth threshold corresponding to a distance away from the lens surface.

14. The system of claim 13, wherein the depth threshold is no greater than 1.8 centimeters.

* * * * *